United States Patent [19]

Alt

[11] Patent Number: 4,761,176

[45] Date of Patent: Aug. 2, 1988

[54] HERBICIDAL 2-HALOACETANILIDES

[75] Inventor: Gerhard H. Alt, University City, Mo.

[73] Assignee: Monsanto Company, St. Louis, Mo.

[21] Appl. No.: 589,983

[22] Filed: Mar. 15, 1984

Related U.S. Application Data

[63] Continuation of Ser. No. 133,696, Mar. 25, 1980, abandoned.

[51] Int. Cl.$^4$ .............................................. A01N 37/24
[52] U.S. Cl. ....................................... 71/118; 564/214
[58] Field of Search ........................... 71/118; 564/214

[56] References Cited

U.S. PATENT DOCUMENTS

| | | | |
|---|---|---|---|
| 3,442,945 | 5/1969 | Olin | 564/214 |
| 3,547,620 | 12/1970 | Olin | 71/118 |
| 4,152,137 | 5/1979 | Martin | 71/118 |

*Primary Examiner*—Catherine L. Mills
*Attorney, Agent, or Firm*—William I. Andress

[57] ABSTRACT

The disclosure herein relates to a group of N-hydrocarbyloxymethyl-2-haloacetanilide compounds, herbicidal compositions containing said compounds as the active ingredient and herbicidal method of use in various crops, particularly sugarbeets. The herbicides herein are particularly effective against annual grasses, including hard-to-kill narrowleaf weeds such as blackgrass, wild oats, and downy brome and other prevalent grasses such as yellow foxtail, barnyardgrass, crabgrass, annual rye, etc.

14 Claims, No Drawings

HERBICIDAL 2-HALOACETANILIDES

This is a continuation of application Ser. No. 133,696, filed Mar. 25, 1980 abandoned.

BACKGROUND OF THE INVENTION

1. Field of the Invention

This invention pertains to the field of 2-haloacetanilides and their use in the agronomic arts, e.g., as herbicides.

2. Description of the Prior Art

The prior art relevant to this invention includes numerous disclosures of 2-haloacetanilides which may be unsubstituted or substituted with a wide variety of substituents on the anilide nitrogen atom and on the anilide ring including alkyl, alkoxy, alkoxyalkyl, halogen, etc., radicals.

As relevant to the invention compounds, which are characterized by having an alkoxymethyl or alkenyloxymethyl radical on the anilide nitrogen, an alkoxy radical in one ortho position and a specific alkyl radical in the other ortho position, the closest prior art known to the inventor are U.S. Pat. Nos. 3,442,945 and 3,547,620. The most relevant disclosures in the '945 and '620 patents are the compounds 2'-tert-butyl-2-chloro-N-methoxymethyl-6'-methoxyacetanilide and its bromo analog (Examples 18 and 34 of the '620 patent and Examples 18 and 36 of the '945 patent, respectively).

U.S. Pat. Nos. 4,070,389 and 4,152,137 disclose generic formulae which encompass compounds of the type disclosed in said '945 and '620 patents. However, the only disclosed species compound having an alkyl radical in one ortho position and an alkoxy radical in the other ortho position has an alkoxyethyl radical on the anilide nitrogen atom; compounds of this type are discussed in more detail below.

Other less-relevant prior art are Belgian Pat. No. 810,763 and German Application No. 2,402,983; the compounds of these references include compounds of the type disclosed in said '389 and '137 patents and are characterized by an alkoxyalkyl radical having two or more carbon atoms between the anilide nitrogen atom and the oxygen atom of the alkoxy moiety. The most relevant specific disclosures in said Belgian '763 patent and German '983 application appear to be compounds having an ethoxyethyl radical on the anilide nitrogen atom, a methoxy or ethoxy radical in one ortho position and a methyl, ethyl or isopropyl radical in the other ortho position; referring to the '763 patent, see Compound Numbers 7, 13, 18-20 and 26; other less-relevant homologs of these compounds are also disclosed, e.g., Compounds 6, 9, 16 and 17, which have methoxyethyl or methoxypropyl radicals substituted on the nitrogen atom and a methoxy or ethoxy radical in one ortho position and a methyl radical in the otner ortho position.

The above '945 patent contains some herbicidal data relative to those above-mentioned compounds having a chemical configuration most closely related to the invention compounds, and some data are presented for other homologous and analogous compounds less-closely related in chemical structure, e.g., said Compound Numbers 6 and 9 in said '763 patent. More particularly, these most relevant references, while disclosing herbicidal activity on a variety of weeds, do not disclose any data for any compounds which are shown to additionally and/or simultaneously control the hard-to-kill narrowleaf weeds, blackgrass, wild oats and downy brome and other weeds such as yellow foxtail, annual rye, barnyardgrass and crabgrass, although said Belgian '763 patent presents data showing good control of wild oats and undefined species of various other weeds in sugar beets. However, as will be shown herein, compounds according this invention possess unexpectedly superior properties as selective herbicides in sugarbeets vis-a-vis the homologous compounds of the prior art.

A further disadvantage of many prior art herbicides is limitation of their use in specified types of soil, i.e., while some herbicides are effective in soils having small amounts of organic matter, they are ineffective in other soils high in organic matter or vice-versa. It is, therefore, advantageous that a herbicide be useful in all types of soil ranging from light organic to heavy clay and muck.

Yet another disadvantage of some prior art herbicides is the lack of weed control persistence under heavy rainfall which results in leaching of the herbicide.

And, finally, a disadvantage in some herbicides is the necessity to adopt and maintain special handling procedures due to the toxic nature thereof. Hence, a further desideratum is that a herbcide be safe to handle.

It is, therefore, an object of this invention to provide a group of herbicidal compounds which overcome the above-mentioned disadvantages of the prior art and provide a multiplicity of advantages for a single group of herbicides.

It is an object of this invention to provide herbicides which selectively control various weeds, particularly annual grasses, including hard-to-kill narrowleaf weeds such as blackgrass, wild oats and downy brome and other annual grasses such as yellow foxtail, barnyardgrass, crabgrass and annual rye, particularly. in sugarbeets.

Still another object of this invention is the provision of herbicides which are effective over a wide range of soils, e.g., ranging from light-medium organic to heavy clay and muck.

Another object of this invention is the provision of herbicides which are resistant to leaching under heavy rainfall.

Finally, it is an advantage of the herbicides of this invention that they are safe and require no special handling procedures.

The above and other objects of the invention will become more apparent from the detailed description below.

SUMMARY OF THE INVENTION

The present invention relates to herbicidally active compounds, herbicidal compositions containing these compounds as active ingredients and herbicidal method of use of said compositions in particular crops.

It has now been found that a selective group of 2-haloacetanilides characterized by specific combinations of alkoxymethyl or alkenyloxymethyl radicals on the anilide nitrogen atom, specific alkoxy radicals in one ortho position and a $C_{1-3}$ alkyl, i.e., methyl, ethyl or isopropyl radical in the other ortho position possess unexpectedly superior and outstanding selective herbicidal properties as sugarbeet herbicides vis-a-vis prior art herbicides, including homologous compounds of the most relevant prior art.

A primary feature of the herbicidal compositions of this invention is their ability to control narrowleaf weeds in sugarbeets, particularly the hard-to-kill species such as wild oats and blackgrass, as well as less-resistant species such as yellow foxtail, barnyardgrass, crabgrass and other noxious weeds.

The compounds of this invention are characterized by the formula

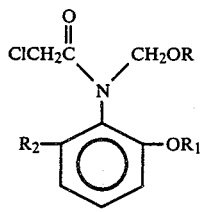

wherein

R is ethyl, n-propyl, isopropyl, isobutyl, allyl or butenyl;

$R_1$ is methyl, n-propyl, isopropyl, n-butyl, isobutyl or isoamyl and $R_2$ is methyl, ethyl or isopropyl; provided that:
when $R_2$ is isopropyl, R is ethyl and $R_1$ is n-butyl;
when $R_2$ is ethyl, R is ethyl, n-propyl or allyl and $R_1$ is n-butyl or isobutyl;
when R is n-propyl or isopropyl, $R_1$ is isobutyl;
when R is isobutyl, $R_1$ is n-propyl, isopropyl, isobutyl or isoamyl and
when R is butenyl, $R_1$ is methyl.

Compounds of particular interest and utility herein are those wherein in the above formula R is a $C_{2-4}$ alkyl radical, preferably ethyl, n-propyl or allyl, $R_1$ is a $C_3$ or $C_4$ alkyl, especially n-butyl or isobutyl and $R_2$ is methyl or ethyl.

Particular species of compounds according to this invention are:

N-(isobutoxymethyl)-2′-isopropoxy-6′-methyl-2-chloroacetanilide;

N-(isobutoxymethyl)-2′-isoamyloxy-6′-methyl-2-chloroacetanilide;

N-(n-propoxymethyl)-2′-isobutoxy-6′-methyl-2-chloroacetanilide;

N-(ethoxymethyl)-2′-n-butoxy-6′-isopropyl-2-chloroacetanilide;

N-(isobutoxymethyl)-2′-isobutoxy-6′-methyl-2-chloroacetanilide;

N-(isopropoxymethyl)-2′-isobutoxy-6′-methyl-2-chloroacetanilide;

N-(isobutoxymethyl)-2′-n-propoxy-6′-methyl-2-chloroacetanilide;

N-(2-buten-1-yloxymethyl)-2′-methoxy-6′-methyl-2-chloroacetanilide;

N-(n-propoxymethyl)-2′-n-butoxy-6′-ethyl-2-chloroacetanilide;

N-(allyloxymethyl)-2′-n-butoxy-6′-ethyl-2-chloroacetanilide;

N-(ethoxymethyl)-2′-isobutoxy-6′-ethyl-2-chloroacetanilide; and

N-(allyloxymethyl)-2′-isobutoxy-6′-ethyl-2-chloroacetanilide.

The utility of the compounds of this invention as the active ingredient in herbicidal compositions formulated therewith and the method of use thereof will be described below.

DETAILED DESCRIPTION OF THE INVENTION

The compounds of this invention may be made in a variety of ways. For example, these compounds may be prepared by the azomethine route described in the above-mentioned U.S. Pat. Nos. 3,442,945 and 3,547,620. According to the azomethine process, the appropriate primary aniline is reacted with formaldehyde to obtain the corresponding methyleneaniline (substituted phenylazomethine), which is then reacted with a haloacetylating agent such as chloroacetyl chloride or chloroacetyl anhydride which, in turn, is reacted with the appropriate alcohol to obtain the corresponding N-alkoxymethyl-2-chloroacetanilide as the final product.

Another process for producing compounds according to this invention involves an N-alkylation of the anion of the appropriate secondary 2-haloacetanilide with an alkylating agent under basic conditions. The N-alkylation process is described in more detail in U.S. Ser. No. 63,005, filed Aug. 2, 1979, now U.S. Pat. No. 4,258,196 assigned to the same assignee herein. Example 1 below illustrates the use of said N-alkylation to prepare one species of this invention. A modified N-alkylation process is described in Example 2 for preparing another species of the invention. The modified N-alkylation process described in Example 2 herein involves the in situ preparation of halomethyl alkyl or alkenyl ethers used as starting materials in the N-alkylation process. The modified N-alkylation process is the invention of another inventive entity of the assignee of this application and is described in more detail in application U.S. Ser. No. 133,720, filed of even date herewith now U.S. Pat. No 4,284,564.

EXAMPLE 1

2′-isobutoxy-6′-methyl-2-chloroacetanilide, 5.6 g (0.022 mol), chloromethyl-n-propyl ether, 4.75 g (0.44 mol) and 2.0 g of benzyl triethylammonium chloride were mixed in 250 ml of methlyene chloride and chilled. To the mixture at 15° C. ml of was added 50 ml of 50% NaOH all at one and stirred for 2 hours, then 100 ml of cold water was added. The layers were separated, washed with water, then dried over $MgSO_4$ and evaporated by Kugelrohr to obtain 6.5 g (90% yield) of clear oil, b.p. 130° C. at 0.04 mm Hg.

Anal. Calc'd for $C_{17}H_{26}ClNO_3$ (%): C, 62.28; H, 7.99; Cl, 10.81; Found: C, 62.27; H, 8.01; Cl, 10.81.

The product was identified as N-(n-propoxymethyl)-2′-isobutoxy-6′-methyl-2-chloroacetanilide.

EXAMPLE 2

This example describes a modification of the N-alkylation process described in Example 1. In this process embodiment, the alkylating agent is formed in situ, thus effecting a more efficient, economic and simple operation.

To a chilled mixture of 4.6 g (0.1 mol) of ethanol, 1.5 g (0.05 mol) of anhydrous paraformaldehyde and 100 ml of methylene chloride were added 6.1 g (0.05 mol) of acetyl bromide; the mixture was stirred until all the paraformaldehyde was dissolved. To the mixture was then added 5.1 g (0.018 mol) of 2′-n-butoxy-6′-isopropyl-2-chloroacetanilide, 2.0 g of benzyl triethylammonium chloride and 40 ml of methylene chloride. The mixture was cooled to 15° C. and 50 ml of 50% NaOH added all at once and stirred for 2 hours. The layers were separated, washed with water, dried over $MgSO_4$ and evaporated by Kugelrohr to obtain 4.6 g (77% yield) of yellow liquid, b.p. 125° C. at 0.07 mmHg.

Anal. Calc'd for $C_{18}H_{28}ClNO_3$ (%): C, 63.24; H, 8.26; Cl, 10.37; Found: C, 63.23; H, 8.29; Cl, 10.37.

The product was identified as N-(ethoxymethyl)-2'-n-butoxy-6'-isopropyl-2-chloroacetanilide.

EXAMPLES 3-12

Following substantially the same procedure and conditions described in Examples 1 or 2, but substituting the appropriate secondary anilide and alkylating agent as starting materials and quantities thereof, the corresponding N-(alkoxymethyl or alkenyloxymethyl)-2-haloacetanilides were prepared; these compounds are identified in Table I, together with certain physical properties.

TABLE I

| Example No. | Compound | Empirical Formula | B.P. °C. (mm Hg) | Element | Analysis Calculated | Found |
|---|---|---|---|---|---|---|
| 3 | N—(isobutoxymethyl)-2'-isobutoxy-6'-methyl-2-chloroacetanilide | $C_{18}H_{28}ClNO_3$ | 115 (0.02) | C<br>H<br>Cl | 63.24<br>8.26<br>10.37 | 63.19<br>8.30<br>10.38 |
| 4 | N—(isopropoxymethyl)-2'-isobutoxy-6'-methyl-2-chloroacetanilide | $C_{17}H_{26}ClNO_3$ | 120 (0.03) | C<br>H<br>Cl | 62.28<br>7.99<br>10.81 | 62.26<br>7.99<br>10.81 |
| 5 | N—(2-buten-1-oxymethyl)-2'-methoxy-6'-methyl-2-chloroacetanilide | $C_{15}H_{20}ClNO_3$ | 114 (0.03) | C<br>H<br>Cl | 60.50<br>6.77<br>11.91 | 60.38<br>6.83<br>11.85 |
| 6 | N—(isobutoxymethyl)-2'-isopropoxy-6'-methyl-2-chloroacetanilide | $C_{17}H_{26}ClNO_3$ | — | C<br>H<br>N<br>Cl | 62.28<br>7.99<br>4.27<br>10.81 | 62.33<br>8.04<br>4.27<br>10.82 |
| 7 | N—(isobutoxymethyl)-2'-isobutoxy-6'-methyl-2-chloroacetanilide | $C_{19}H_{30}ClNO_3$ | 120 (0.025) | C<br>H<br>Cl | 64.12<br>8.50<br>9.96 | 63.98<br>8.57<br>10.03 |
| 8 | N—(isobutoxymethyl)-2'-n-propoxy-6'-methyl-2-chloroacetanilide | $C_{17}H_{26}ClNO_3$ | 127 (0.08) | C<br>H<br>Cl | 62.28<br>7.99<br>10.81 | 62.20<br>8.06<br>10.88 |
| 9 | N—(n-propoxymethyl)-2'-n-butoxy-6'-ethyl-2-chloroacetanilide | $C_{18}H_{28}ClNO_3$ | 117 (0.02) | C<br>H<br>Cl | 63.24<br>8.26<br>10.37 | 63.31<br>8.27<br>10.42 |
| 10 | N—(allyloxymethyl)-2'-n-butoxy-6'-ethyl-2-chloroacetanilide | $C_{18}H_{26}ClNO_3$ | 123 (0.04) | C<br>H<br>Cl | 63.61<br>7.71<br>10.43 | 63.60<br>7.74<br>10.42 |
| 11 | N—(ethoxymethyl)-2'-isobutoxy-6'-ethyl-2-chloroacetanilide | $C_{17}H_{26}ClNO_3$ | 132 (0.07) | C<br>H<br>Cl | 62.28<br>7.99<br>10.81 | 62.27<br>8.02<br>10.82 |
| 12 | N—(allyloxymethyl)-2'-isobutoxy-6'-ethyl-2-chloroacetanilide | $C_{18}H_{26}ClNO_3$ | 124 (0.02) | C<br>H<br>Cl | 63.61<br>7.71<br>10.43 | 63.61<br>7.71<br>10.45 |

The secondary anilide starting materials used in the above examples are prepared according to known methods, e.g., by haloacetylation of the corresponding primary amine with such haloacetylation agents as a haloacetyl halide or anhydride. Typically, the appropriate quantity of the appropriate primary amine is dissolved in a solvent such as methylene chloride containing a base, e.g., 10% NaOH, and stirred vigorously while mixing with a solution of the haloacetyl halide, e.g., chloroacetyl chloride, under external cooling, e.g., at 15°-25° C. The layers are separated and the organic solvent layer washed with water, dried and evaporated in vacuo.

The primary amines used to prepare the secondary anilides also may be prepared by known means, e.g., by catalytic reduction of the corresponding appropriately-substituted nitrobenzene, e.g., 2-alkoxy-6-alkyl nitrobenzene, in a solvent such as an alcohol, e.g., ethanol, using platinum oxide catalyst.

As noted above, the compounds of this invention have been found to be effective as herbicides, particularly as pre-emergence herbicides, although post-emergence activity has also been shown. The preemergence tests referred to herein include both greenhouse and field tests. In the greenhouse tests, the herbicide is applied either as a surface application after planting the seeds or vegetative propagules or by incorporation into a quantity of soil to be applied as a cover layer over the test seeds in pre-seeded test containers. In the field tests, the herbicide may be applied by pre-plant incorporated ("P.P.I.") into the soil, i.e., the herbicide is applied to the surface of the soil, then incorporated therein by mixing means followed by planting of the crop seeds, or the herbicide may be applied to the surface ("S.A.", surface application) after the crop seed is planted.

The surface application ("S.A") test method used in the greenhouse is performed as follows: Containers, e.g., aluminum pans typically 9.5"×5.25"×2.75" (24.13 cm×13.34 cm×6.99 cm) or plastic pots 3.75"×3.75"×3" (9.53 cm×9.53 cm×7.62 cm) having drain holes in the bottom, are level-filled with Ray silt loam soil then compacted to a level 0.5 inch (1.27 cm) from the top of the pots. The pots are then seeded with plant species to be tested, covered with a 0.5 inch layer of the test soils. The herbicide is then applied to the surface of the soil, e.g., with a belt sprayer at 20 gal/A, 30 psi (187 1/ha, 2.11 kg/cm$^2$). Each pot receives 0.25 inch (0.64 cm) water as overhead irrigation and the pots are then placed on greenhouse benches for subsequent sub-irrigation as needed. As an alternative procedure, the overhead irrigation may be omitted. Observations of herbicidal effects are made about three weeks after treatment.

The herbicide treatment by soil incorporation ("S.I.") used in the greenhouse tests are as follows:

A good grade of top soil is placed in aluminum pans and compacted to a depth of three-eighths to one-half inch from the top of the pan. On tne top of the soil is placed a predetermined number of seeds or vegetative propagules of various plant species. The soil required to level fill the pans after seeding or adding vegetative propagules is weighed into a pan. The soil and a known amount of the active ingredient applied in a solvent or as a wettable powder suspension are thoroughly mixed, and used to cover the prepared pans. After treatment, the pans are given an initial overhead irrigation of water, equivalent to one-fourth inch (0.64 cm) rainfall, then watered by subirrigation as need to give adequate moisture for germination and growth. As an alternative procedure, the overhead irrigation may be omitted. Observations are made about 2-3 weeks after seeding and treatment.

Tables II and III summarize results of tests conducted to determine the preemergence herbicidal activity of the compounds of this invention; in these tests, the herbicides were applied by soil incorporation and sub-irrigation watering only; a dash (—) means that the indicated plant was not tested. The herbicidal rating was obtained by means of a fixed scale based on the percent injury of each plant species. The ratings are defined as follows:

| % Control | Rating |
| --- | --- |
| 0-24 | 0 |
| 25-49 | 1 |
| 50-74 | 2 |
| 75-100 | 3 |

The plant species utilized in one set of tests, the data for which are shown in Table II, are identified by letter in accordance with the following legend:

| A | Canada Thistle | G | Yellow Nutsedge |
| --- | --- | --- | --- |
| B | Cocklebur | H | Quackgrass |
| C | Velvetleaf | I | Johnsongrass |
| D | Morningglory | J | Downy Brome |
| E | Lambsquarters | K | Barnyardgrass |
| F | Smartweed | | |

TABLE II

| Compound of Example No. | kg/ha | Pre-Emergent Plant Species | | | | | | | | | | |
| --- | --- | --- | --- | --- | --- | --- | --- | --- | --- | --- | --- | --- |
| | | A | B | C | D | E | F | G | H | I | J | K |
| 1 | 11.2 | 3 | 1 | 2 | 2 | 3 | 3 | 3 | 3 | 3 | 3 | 3 |
| | 5.6 | 3 | 0 | 2 | 2 | 3 | 2 | 3 | 3 | 3 | 3 | 3 |
| 2 | 11.2 | 1 | 1 | 2 | 2 | 3 | 3 | 3 | 3 | 3 | 3 | 3 |
| | 5.6 | 0 | — | 2 | 1 | 3 | 2 | 3 | 3 | 3 | 3 | 3 |
| | 1.12 | 0 | — | 1 | 0 | 1 | 1 | 2 | 1 | 0 | 3 | 3 |
| 3 | 11.2 | 0 | 0 | 0 | 3 | 2 | 3 | 3 | 3 | 1 | 3 | 3 |
| | 5.6 | 0 | 0 | 0 | 0 | 2 | 1 | 1 | 3 | 3 | 3 | 3 |
| 4 | 11.2 | 3 | 0 | 2 | 2 | 3 | 3 | 3 | 3 | 2 | 3 | 3 |
| | 5.6 | 2 | 1 | 2 | 2 | 2 | 2 | 3 | 3 | 1 | 3 | 3 |
| 5 | 11.2 | 2 | 1 | 0 | 1 | 3 | 2 | 3 | 3 | 1 | 3 | 3 |
| | 5.6 | 1 | 0 | 0 | 3 | 1 | 1 | 3 | 3 | 0 | 3 | 3 |
| 6 | 11.2 | 2 | 1 | 1 | 1 | 3 | 3 | 3 | 3 | 3 | 3 | 3 |
| | 5.6 | 2 | 1 | 1 | 2 | 3 | 3 | 3 | 3 | 0 | 3 | 3 |
| 7 | 11.2 | 3 | 0 | 1 | 1 | 3 | 2 | 3 | 3 | 0 | 3 | 3 |
| | 5.6 | 2 | 0 | 2 | 1 | 3 | 2 | 3 | 3 | 1 | 3 | 3 |
| 8 | 11.2 | 3 | 1 | 0 | 2 | 3 | 3 | 3 | 3 | 3 | 3 | 3 |
| | 5.6 | 3 | 2 | 0 | 2 | 3 | 3 | 3 | 3 | 3 | 3 | 3 |
| 9 | 11.2 | 3 | 0 | 0 | 0 | 2 | 1 | 3 | 2 | 1 | 3 | 3 |
| | 5.6 | 3 | 1 | 0 | 0 | 2 | 1 | 3 | 2 | 0 | 3 | 3 |
| 10 | 11.2 | — | 0 | 1 | 1 | 2 | 2 | 3 | 3 | 3 | 3 | 3 |
| | 5.6 | — | 0 | 0 | 0 | 3 | 2 | 2 | 3 | 3 | 3 | 3 |
| 11 | 11.2 | 3 | 1 | 2 | 2 | 3 | 2 | 3 | 3 | 3 | 3 | 3 |
| | 5.6 | 2 | 1 | 2 | 2 | 3 | 2 | 3 | 3 | 1 | 3 | 3 |
| 12 | 11.2 | 3 | — | 0 | 1 | 3 | 3 | 3 | 3 | 3 | 3 | 3 |
| | 5.6 | 2 | 0 | 1 | 1 | 1 | 1 | 3 | 2 | 1 | 3 | 3 |

The compounds were further tested by utilizing the above procedure on the following plant species:

| L | Soybean | R | Hemp sesbania |
| --- | --- | --- | --- |
| M | Sugarbeet | E | Lambsquarters |
| N | Wheat | F | Smartweed |
| O | Rice | C | Velvetleaf |
| P | Sorghum | J | Downy brome |
| B | Cocklebur | S | Panicum Spp. |
| Q | Wild Buckwheat | K | Barnyardgrass |
| D | Morningglory | T | Crabgrass |

The results are summarized in Table III.

TABLE III

| Compound of Example No. | kg/h | Pre-Emergent Plant Species | | | | | | | | | | | | | | |
| --- | --- | --- | --- | --- | --- | --- | --- | --- | --- | --- | --- | --- | --- | --- | --- | --- |
| | | L | M | N | O | P | B | Q | D | R | E | F | C | J | S | K | T |
| 1 | 5.6 | 1 | 3 | 3 | 3 | 3 | 0 | 3 | 0 | 3 | 3 | 3 | 1 | 3 | 3 | 3 | 3 |
| | 1.12 | 0 | 1 | 0 | 3 | 3 | 0 | 1 | 0 | 1 | 3 | 2 | 0 | 3 | 3 | 3 | 3 |
| | 0.28 | 0 | 0 | 0 | 2 | 3 | 0 | 2 | 0 | 0 | 0 | 1 | 0 | 3 | 3 | 3 | 3 |
| | 0.06 | 0 | 0 | 0 | 2 | 2 | 0 | 0 | 0 | 1 | 0 | 0 | 0 | 3 | 2 | 3 | 3 |
| | 0.01 | 0 | 0 | 0 | 1 | 0 | 0 | 0 | 0 | — | 2 | 1 | 0 | 0 | 0 | 2 | 3 |
| 2 | 5.6 | 1 | 2 | 3 | 3 | 3 | 3 | 2 | 3 | 2 | 2 | 3 | 1 | 3 | 3 | 3 | 3 |
| | 1.12 | 0 | 1 | 2 | 3 | 3 | 0 | 0 | 1 | 2 | 2 | 2 | 0 | 3 | 3 | 3 | 3 |
| | 0.28 | 0 | 0 | 2 | 2 | 2 | 0 | 0 | 0 | 0 | 1 | 1 | 0 | 3 | 2 | 3 | 3 |
| | 0.06 | 0 | 0 | 0 | 1 | 0 | 0 | 0 | 0 | — | 0 | 0 | 0 | 1 | 1 | 3 | 1 |
| | 0.01 | 0 | 0 | 0 | 0 | 0 | — | 0 | 0 | 0 | 0 | 0 | 0 | 0 | 0 | 1 | 0 |
| 3 | 5.6 | 0 | 1 | 2 | 2 | 3 | 0 | 0 | 3 | 2 | 0 | 0 | 0 | 3 | 3 | 3 | 3 |
| | 1.12 | 0 | 0 | 1 | 3 | 3 | 0 | 0 | 0 | 0 | 0 | 0 | 0 | 3 | 3 | 3 | 3 |
| | 0.28 | 0 | 0 | 0 | 0 | 0 | 0 | 0 | 0 | 0 | 0 | 0 | 0 | 1 | 1 | 3 | 3 |
| | 0.06 | 0 | 0 | 0 | 0 | 0 | 0 | 0 | 1 | 0 | 0 | 0 | 0 | 0 | 1 | 1 | 2 |
| 4 | 5.6 | 1 | 2 | 3 | 3 | 3 | 0 | 1 | 1 | 3 | 2 | 1 | 1 | 3 | 3 | 3 | 3 |
| | 1.12 | 0 | 1 | 3 | 3 | 3 | 0 | 0 | 1 | 3 | 1 | 0 | 0 | 3 | 3 | 3 | 3 |
| | 0.28 | 0 | 1 | 1 | 2 | 3 | 0 | 0 | 0 | 0 | 0 | 0 | 0 | 2 | 3 | 3 | 3 |
| | 0.06 | 0 | 0 | 0 | 1 | 1 | 0 | 0 | 0 | 0 | 0 | 0 | 0 | 1 | 1 | 3 | 3 |
| | 0.01 | 0 | 0 | 0 | 0 | 0 | 0 | 0 | 0 | — | 0 | 0 | 0 | 1 | 0 | 1 | 2 |
| | 0.006 | 0 | 0 | 0 | 0 | 0 | 0 | 0 | 0 | 0 | 0 | 0 | 0 | 0 | 0 | 1 | 1 |
| 5 | 5.6 | 2 | 2 | 3 | 3 | 3 | 2 | 2 | 3 | 3 | 2 | 2 | 0 | 3 | 3 | 3 | 3 |
| | 1.12 | 0 | 2 | 2 | 3 | 3 | 3 | 3 | 2 | 2 | 2 | 2 | 0 | 3 | 3 | 3 | 3 |
| | 0.28 | 0 | 1 | 1 | 3 | 1 | 3 | 3 | 3 | 1 | 1 | 0 | 0 | 3 | 3 | 3 | 3 |
| | 0.06 | 0 | 1 | 0 | 0 | 0 | 1 | 0 | 3 | 2 | 0 | 0 | 0 | 2 | 1 | 3 | 3 |
| | 0.01 | 0 | 1 | 0 | 0 | 0 | 0 | 0 | 0 | 0 | 0 | 0 | 0 | 0 | 0 | 3 | 3 |
| 6 | 5.6 | 1 | 2 | 3 | 3 | 3 | 1 | 2 | 0 | 2 | 3 | 3 | 0 | 3 | 3 | 3 | 3 |
| | 1.12 | 0 | 1 | 1 | 1 | 3 | 0 | 3 | 0 | 0 | 3 | 3 | 0 | 3 | 3 | 3 | 3 |
| | 0.28 | 0 | 1 | 1 | 1 | 2 | 0 | 0 | 0 | 0 | 0 | 0 | 0 | 1 | 2 | 3 | 3 |

TABLE III-continued

| Compound of Example No. | kg/h | \multicolumn{16}{c}{Pre-Emergent Plant Species} |
|---|---|---|---|---|---|---|---|---|---|---|---|---|---|---|---|---|---|

| Compound of Example No. | kg/h | L | M | N | O | P | B | Q | D | R | E | F | C | J | S | K | T |
|---|---|---|---|---|---|---|---|---|---|---|---|---|---|---|---|---|---|
|  | 0.06 | 0 | 0 | 0 | 0 | 0 | 0 | 0 | 0 | 0 | 0 | 0 | 0 | 0 | 0 | 2 | 2 |
| 7 | 5.6 | 0 | 2 | 3 | 3 | 3 | 2 | 2 | 2 | 3 | 3 | 0 | 3 | 3 | 3 | 3 | 3 |
|  | 1.12 | 0 | 1 | 1 | 2 | 2 | 0 | 2 | 0 | 3 | 2 | 0 | 3 | 2 | 3 | 3 | 3 |
|  | 0.28 | 0 | 1 | 0 | 1 | 0 | 0 | 0 | 0 | 0 | 0 | 0 | 1 | 1 | 3 | 3 |
|  | 0.06 | 0 | 1 | 0 | 0 | 0 | 0 | — | 0 | 0 | 1 | 0 | 0 | 1 | 2 | 1 | 2 |
| 8 | 5.6 | 2 | 2 | 3 | 3 | 3 | 2 | 2 | 2 | 3 | 3 | 3 | 0 | 3 | 3 | 3 | 3 |
|  | 1.12 | 0 | 1 | 1 | 1 | 3 | 1 | 2 | 1 | 3 | 2 | 2 | 0 | 3 | 3 | 3 | 3 |
|  | 0.28 | 0 | 0 | 0 | 0 | 1 | 0 | 0 | 0 | 1 | 3 | 2 | 0 | 1 | 3 | 3 | 3 |
|  | 0.06 | 0 | 1 | 0 | 0 | 1 | — | 1 | 0 | 1 | 0 | 1 | 0 | 0 | 0 | 3 | 3 |
|  | 0.01 | 1 | 0 | 0 | 0 | 0 | 1 | 0 | 0 | 0 | 0 | 0 | 0 | 0 | 0 | 2 | 3 |
| 9 | 5.6 | 1 | 2 | 3 | 3 | 3 | 0 | 3 | 1 | 2 | 3 | 3 | 0 | 3 | 3 | 3 | — |
|  | 1.12 | 0 | 0 | 2 | 3 | 2 | 0 | 2 | 0 | 2 | 0 | 1 | 0 | 3 | 3 | 3 | — |
|  | 0.28 | 0 | 0 | 0 | 1 | 1 | 0 | 0 | 0 | 0 | 0 | 0 | 0 | 3 | 3 | 3 | — |
|  | 0.06 | 0 | 0 | 0 | 0 | 0 | 0 | 0 | 0 | 0 | 0 | 0 | 0 | 1 | 0 | 3 | — |
|  | 0.01 | 0 | 0 | 0 | 0 | 0 | 0 | 0 | 0 | 0 | 0 | 0 | 0 | 1 | 0 | 0 | — |
| 10 | 5.6 | 0 | 2 | 3 | 3 | 3 | 0 | 3 | 0 | 1 | 3 | 3 | 1 | 3 | 3 | 3 | — |
|  | 1.12 | — | 1 | 2 | 2 | 1 | 0 | 1 | 1 | 0 | 2 | 1 | 0 | 3 | 3 | 3 | — |
|  | 0.28 | 0 | 1 | 1 | 2 | 1 | 0 | 0 | 0 | 0 | 1 | 0 | 0 | 3 | 3 | 3 | — |
|  | 0.06 | 0 | 0 | 0 | 0 | 0 | 0 | 0 | 0 | 0 | 0 | 1 | 0 | 0 | 0 | 3 | — |
|  | 0.01 | 0 | 0 | 0 | 0 | 0 | 0 | 0 | 0 | 0 | 0 | 0 | 0 | 0 | 0 | 0 | — |
| 11 | 5.6 | 1 | 2 | 3 | 3 | 3 | 1 | 2 | 3 | 3 | 3 | 3 | 2 | 3 | 3 | 3 | — |
|  | 1.12 | 0 | 1 | 3 | 3 | 3 | 0 | 2 | 1 | 3 | 2 | 2 | 2 | 3 | 3 | 3 | — |
|  | 0.28 | 0 | 1 | 2 | 2 | 2 | 0 | 1 | 0 | 3 | 2 | 0 | 0 | 3 | 3 | 3 | — |
|  | 0.06 | 0 | 0 | 0 | 1 | 0 | 0 | 0 | 0 | 0 | 1 | 5 | 0 | 3 | 1 | 3 | — |
|  | 0.01 | 0 | 0 | 0 | 1 | 0 | — | 0 | 0 | 3 | 0 | — | 0 | 0 | 0 | 0 | — |
| 12 | 5.6 | 0 | 3 | 3 | 3 | 3 | 1 | 3 | 1 | 3 | 3 | 3 | 1 | 3 | 3 | 3 | 3 |
|  | 1.12 | 0 | 1 | 3 | 3 | 3 | 0 | 2 | 0 | 2 | 2 | 1 | 0 | 3 | 3 | 3 | 3 |
|  | 0.28 | 0 | 1 | 2 | 1 | 0 | 0 | 1 | 0 | 0 | 2 | 3 | 0 | 3 | 3 | 3 | 3 |
|  | 0.06 | 0 | 0 | 1 | 1 | 0 | 0 | 0 | 0 | 0 | 2 | 3 | 0 | 1 | 0 | 3 | 3 |
|  | 0.01 | 0 | 0 | 0 | 0 | 0 | 0 | 0 | 0 | 0 | 2 | 3 | 0 | 1 | 0 | 1 | 1 |

The herbicides of this invention have been found to possess unexpectedly superior properties as selective pre-emergence herbicides for use in sugarbeets, most particularly in the selective control of hard-to-kill narrowleaf weeds, including blackgrass, wild oats and downy brome and other weeds such as yellow foxtail, annual rye, barnyardgrass and large crabgrass. Selective control and suppression of the above-mentioned and other weeds with the invention herbicides has been found in a variety of other crops including soybeans, cotton, peanuts, snap beans (bush beans), rape, cucumber and tomatoes. However, the markedly outstanding herbicidal properties of the invention compounds are most manifest in their selective control of annual grasses in sugarbeets.

In order to illustrate the unexpectedly superior properties of the compounds of this invention both on an absolute basis and on a relative basis, comparative tests were conducted in the greenhouse with: (1) homologous compounds of the prior art most closely related in chemical structure to the invention compounds and (2) other compounds, which though not homologs, fall within the scope of said prior art and one of which has superior properties as a sugarbeet herbicide and two of which are commercial herbicides. All of the compounds in the comparative tests below are generically defined as substituted phenyl-N-hydrocarbyloxyalkyl-2-haloacetanilides. As used in the tables of data herein the compared prior art compounds are identified as follows:

A.  N-(methoxymethyl)-2'-methoxy-6'-tert-butyl-2-chloroacetanilide. (Example 18, U.S. Pat. Nos. 3,442,945 and 3,547,620).

B.  N-(methoxymethyl)-2'-methoxy-6'-tert-butyl-2-bromoacetanilide. (Example 34 of said '620 patent and Example 36 of said '945 patent).

C. N-(isobutoxymethyl)-2',6'-dimethyl-2-chloroacetanilide; acetanilide; common name "delachlor". (Example 31 of said '945 patent and Example 24 of said '620 patent).

D.  N-(allyloxymethyl)-2',6'-dimethyl-2-chloroacetanilide. (Example 47 of said '620 patent).

E.  N-(methoxymethyl)-2',6'-diethyl-2-chloroacetanilide. (Example 5 of said '620 and '945 patents); common name "alachlor", active ingredient in the commercial herbicide LASSO ®, registered trademark of Monsanto Company.

F.  N-(methoxyethyl)-2'-methoxy-6'-methyl-2'-chloroacetanilide.. (Compound No. 6 of said Belgian '763 patent; also listed in German Application No. 2,402,983).

G.  N-(ethoxyethyl)-2'-methoxy-6'-methyl-2-chloroacetanilide. (Compound No. 7 in Belgian Pat. No. 810,763).

H.  N-(1-methoxyprop-2-yl)-2'-methoxy-6'-methyl-2-chloroacetanilide. (Compound No. 9 of said Belgian '763 patent).

I.  N-(methoxyethyl)-2'-ethoxy-6'-methyl-2-chloroacetanilide. (Compound No. 16 of said Belgian '763 patent).

J. N-(ethoxyethyl)-2'-ethoxy-6'-methyl-2-choroacetanilide. (Compound No. 18 of said Belgian '763 patent).

K.  N-(methoxyethyl)-2'-methoxy-6'-isopropyl-2-chloroacetanilide. (Compound No. 26 of said Belgian '763 patent).

L.  N-(isopropoxyethyl)-2'-methoxy-6'-methyl-2-chloroacetanilide.

M.  N-(1-methoxyprop-2-yl)-2'-ethyl-6'-methyl-2-chloroacetanilide. (U.S. Pat. No. 3,937,730 and German Application No. 2,402,983); common name "metolachlor", active ingredient in the commercial herbicide "Dual ®", registered trademark of Ciba Geigy Corporation.

Although Compound C above is less similar in structure than the mentioned homologous herbicides in said '945 and '620 patents, in that it lacks an alkoxy substituent in an ortho position, it is included in tests herein because it has shown superior properties as a sugarbeet herbicide vis-a-vis other compounds in said '945 and '620 patents. Similarly, Compounds E and M are included in tests herein because they are within the scope of the indicated relevant prior art and have achieved commercial status. Compounds F-L are included in tests herein because of some similarity of structure relative to certain compounds of this invention.

In pre-emergence herbicidal tests, compounds of this invention were compared with compounds A-M of the prior art with respect to control of various weeds, with emphasis on annual narrowleaf species which are prevalent infestations in sugarbeets. Test results are presented below.

In the discussion of data below, reference is made to herbicide application rates symbolized as "$GR_{15}$" and "$GR_{85}$"; these rates are given in kilograms per hectare (kg/ha) which are convertible into pounds per acre (lbs/A) by dividing the kg/ha rate by 1.12. $GR_{15}$ defines the maximum rate of herbicide required to produce 15% or less crop injury, ano $GR_{85}$ defines the minimum rate required to achieve 85% inhibition of weeds. The $GR_{15}$ and $GR_{85}$ rates are used as a measure of potential commercial performance, it being understood, of course, that suitable commercial herbicides may exhibit greater or lesser plant in injuries within reasonable limits.

A further guide to the effectiveness of a chemical as a selective herbicide is the "selectivity factor" ("SF") for a herbicide in given crops and weeds. The selectivity factor is a measure of the relative degree of crop safety and weed injury and is expressed in terms of the $GR_{15}/GR_{85}$ ratio, i.e., the $GR_{15}$ rate for the crop divided by the $GR_{85}$ rate for the weed, both rates in kg/ha (lb/A). In the tables below, where used, selectivity factors are shown in parenthesis following the weed; the symbol "NS" indicates "non-selective"; A dash (—) after the weed indicates marginal or indeterminant selectivity, e.g., because actual GR15 and/or GR85 rates were higher or lower than the maximum or minimum rates used in the indicated tests.

Since crop tolerance and weed control are interrelated, a brief discussion of this relationship in terms of selectivity factors is meaningful. In general, it is desirable that crop safety factors, i.e., herbicide rolerance values, be high, since higher concentrations of herbicide are frequently desired for one reason or another. Conversely, it is desirable that weed control rates be small, i.e., the herbicide possesses high unit activity, for economical and possibly ecological reasons. However, small rates of application of a herbic:de may not be adequate to control certain weeds and a larger rate may be required. Hence the best herbicides are those which control the greatest number of weeds with the least amount of herbicide and provide the greatest degree of crop safety, i.e., crop tolerance. Accordingly, use is made of selectivity factors (defined above) to quantify the relationship between crop safety and weed control. With reference to the selectivity factors listed in the tables, the higher the numerical value, the greater selectivity of the herbicide for weed control in a given crop.

In the tables below, unless otherwise noted, data for compounds which had been tested in plural runs has been averaged at common rates of application within the range of 0.14 to 2.24 kg/ha (0.125 to 2.0 lb/A). Otherwise, various tables include data from single test runs for application rates down to 0.07 kg/ha (0.0625 lb/A) or up to 4.48 kg/ha (4.0 lb/A).

In a first series of tests, preemergence herbicidal activity data are presented in Table IV comparing the relative efficacy of representative compounds of this invention with relevant compounds of the prior art as selective herbicides against particular weeds commonly associated with sugarbeets. The weeds used in the tests herein have the following abbreviations in the tables: wild oats (WO), barnyardgrass (BYG), large crabgrass (LCG), blackgrass (BG) and yellow foxtail (YFT).

TABLE IV

| Compound | $GR_{15}$ Rate (Kg/Ha) Sugarbeets | $GR_{85}$ Rate (kg/Ha) | | | | |
|---|---|---|---|---|---|---|
| | | WO | BYG | LCG | BG | YFT |
| A | 0.56 | 0.56 (1.0) | 0.14 (4.0) | <0.07 (>8.0) | 0.07 (8.0) | 0.08 (7.0) |
| B | 0.28 | 0.14 (2.0) | <0.07 (>4.0) | <0.07 (>4.0) | 0.07 (4.0) | <0.07 (>4.0) |
| C[a] | 0.84 | 0.08 (1.1) | <0.14 (>6.0) | <0.14 (>6.0) | 0.28 (3.0) | 0.14 (6.0) |
| F | <0.07 | 0.28 (NS) | <0.07 ( — ) | <0.07 ( — ) | 0.14 (NS) | <0.07 ( — ) |
| G | <0.07 | 0.28 (NS) | <0.07 ( — ) | <0.07 ( — ) | 0.07 (NS) | <0.07 ( — ) |
| L | <0.07 | 0.38 (NS) | <0.07 ( — ) | <0.07 ( — ) | 0.07 (NS) | <0.07 ( — ) |
| M[b] | >1.01 | >1.68 (NS) | <0.14 (>7.2) | <0.14 (7.2) | 1.87 (NS) | <0.14 (>7.2) |
| Ex. 1[b] | >2.05 | 0.44 (>4.7) | <0.14 (>14.6) | <0.14 (>14.6) | <0.14 (>14.6) | <0.14 (>14.6) |
| Ex. 3[a] | >2.24 | 0.84 (2.7) | <0.14 (>16.0) | <0.14 (>16.0) | <0.14 (>16.0) | 0.14 (16.0) |
| Ex. 4[a] | 1.54 | 0.70 (2.2) | <0.14 (>11.0) | <0.14 (>11.0) | 0.81 (>1.9) | <0.14 (>11.0) |

[a]Data represent average of two replicates
[b]Data represent average of three replicates Reference to the data in Table IV will show that, with respect to crop safety (as indicated by, the $GR_{15}$ rate for sugarbeets), the invention compounds exhibited outstanding superiority vis-a-vis the prior art compounds. More particularly, with respect to the prior art compounds most closely-related in structure, i.e., compounds A and B having the N-alkoxymethyl-2'-alkoxy-6'-alkyl-2-haloacetanilide configuration, the invention compounds in the test were from 5.8 to greater than 8.0 times safer on sugarbeets than Compound B and from about 2.8 to greater than 4.0 times safer than Compound A. Still more noteworthy, the invention compounds were from 22 to more than 32 times safer on sugarbeets than homologous prior art Compounds F, G and L, each of which caused more than 15% in jury to sugarbeets at the very low rate of less than 0.07 kg/ha.

Although not a homolog of the invention compounds, Compound C is known to have superior properties as a sugarbeet herbicide vis-a-vis other compounds disclosed in the above-mentioned '945 and '620 U.S. patents, which also disclose Compounds A and B. Similarly, although Compound M is not a homolog of the invention compounds, it is within the scope of said German Application No. 2,402,983 which also discloses compounds F and G and generically encompasses Compound L; Compound M is the active ingredient in a commercial herbicide as indicated above. Referring to the $GR_{15}$ rate data in Table IV for Compounds C and M, it will be noted that these compounds exhibited a higher safety factor than the other prior art compounds. However, Compound C was only about one-third to one-half as safe as the invention compounds and Compound M was only about one-half to two-thirds as safe as the invention compounds.

Concomitantly with the indicated high degree of crop safety, the invention compounds exhibited unit activities (i.e., phytotoxicity per unit of herbicide) against the tested weeds (as indicated by $GR_{85}$ rates) more or less comparable to the prior art compounds. The combined high crop safety factor and high unit activity against weeds resulted in outstandingly higher selectivity factors for the invention compounds than for the prior art compounds, with the sole exception of the compound of Example 4 against blackgrass.

Of particular note in Table IV comparing the selectivity factors of the prior art compounds with those of the compound of Example 1 against the respective weeds in sugarbeets, the compound of Example 1 was more selective than the prior art compounds by factors of from about 2.4 to greater than 4.7 fold against wild oats, from about 2.1 to greater than 14.6 fold against barnyardgrass and yellow foxtail and from about 1.8 to greater than 14.6 fold against crabgrass and blackgrass.

Additional tests with selected invention compounds have shown control of barnyardgrass, crabgrass, blackgrass ano yellow foxtail at application rates as low as and even lower than 0.07 kg/ha (0.0625 lb/A). Thus, the compound of Example 1 has exhibited control of each of the foregoing weeds at 0.07 kg/ha or less; the compound of Example 4 has exhibited control of barnyardgrass, crabgrass and yellow foxtail at less than 0.07 kg/ha and the compound of Example 3 has exhibited control of barnyardgrass and crabgrass at 0.07 kg/ha or less.

In other comparative tests, the preemergence herbicidal activities and selectivity factors of prior art Compounds C, E, H and M were determined and compared with those of the compounds of Examples 1-8; the data from these tests are presented in Table V.

higher safety factors, the invention compounds exhibited uniformly and outstandingly superior selectivity factors than the prior art compounds except in isolated instances. Thus, the selectivity factors of Compound C was marginally greater than that of Example 7 against wild oats, somewhat greater than that of the compound of Example 4 and equivalent to that of Example 6 in blackgrass. It will be noted that prior art Compounds E, H and M failed to exhibit crop selectivity against wild oats and blackgrass and the selectivity of Compounds E and H against the remaining weeds was questionable or marginal at best; in any event, the low safety factors of these compounds render them unsuitable as sugarbeet herbicides.

Since the preemergence herbicidal data presented in Tables IV and V were obtained according to identical routine procedures, a comparison of the herbicidal efficacy of the invention compounds in Table IV may also be made against that for the prior art compounds in Table V not listed in Table IV and vice-versa. Here, again, it is clearly demonstrated that each of the invention compounds was outstandingly superior to all of the most relevant prior art compounds in terms of crop safety, without exception, and selective weed control as evidenced by selectivity factors; again, with exceptions in isolated cases. Thus, the selectivity factor of a particular prior art compound against some particular weed may be greater than that of a particular invention compound; but in each such instance, the low sugarbeet safety factor renders the prior art compound unsuitable as a sugarbeet herbicide. For example, the selectivity factor (2.0) of Compound B (Table IV) against wild oats in sugarbeets is greater than that for the compounds of Examples 7 and 8 (1.0 and 1.3, respectively as shown in Table V). However, the safety factors for both of the invention compounds are 8 times greater than that for Compound B in sugarbeets and the selectivity factors of said invention compounds are at least 4 times greater than those of Compound B against barnyardgrass, crabgrass and yellow foxtail and equivalent to that of Compound B abainst blackgrass.

In yet another comparative test of herbicidal efficacy, the compound of Example 1 and Compounds I and J were tested against wild oats, barnyardgrass, large crab-

TABLE V

| Compound | $GR_{15}$ Rate (Kg/Ha) Sugarbeets | $GR_{85}$ Rate (Kg/Ha) | | | | |
|---|---|---|---|---|---|---|
| | | WO | BYG | LCG | BG | YFT |
| C[a] | 0.84 | 0.08 (1.1) | <0.14 (>6.0) | <0.14 (>6.0) | 0.28 (3.0) | 0.14 (6.0) |
| E | <0.14 | 0.56 (NS) | <0.14 (−) | <0.14 (−) | 2.24 (NS) | <0.14 (−) |
| H | <0.14 | 0.86 (NS) | <0.14 (−) | <0.14 (−) | 1.12 (NS) | <0.14 (−) |
| M[b] | >1.01 | >1.68 (NS) | <0.14 (>7.2) | <0.14 (>7.2) | 1.87 (NS) | <0.14 (>7.2) |
| Ex. 1[b] | >2.05 | 0.44 (>4.7) | <0.14 (>14.6) | <0.14 (>14.6) | <0.14 (>14.6) | <0.14 (>14.6) |
| Ex. 2 | 1.12 | 0.56 (2.0) | <0.14 (>8.0) | <0.14 (>8.0) | 0.14 (8.0) | <0.14 (>8.0) |
| Ex. 3[a] | >2.24 | 0.84 (2.7) | <0.14 (>16.0) | <0.14 (>16.0) | <0.14 (>16.0) | <0.14 (>16.0) |
| Ex. 4[a] | 1.54 | 0.70 (2.2) | <0.14 (>11.0) | <0.14 (>11.0) | 0.81 (>1.9) | <0.14 (>11.0) |
| Ex. 5 | 1.12 | 0.42 (>8.0) | <0.14 (>8.0) | <0.14 (>8.0) | 0.42 (>8.0) | <0.14 (>8.0) |
| Ex. 6 | 2.24 | 1.12 (2.0) | <0.14 (>16.0) | <0.14 (>16.0) | 0.38 (3.0) | <0.14 (>16.0) |
| Ex. 7 | 2.24 | 2.24 (1.0) | <0.14 (>16.0) | <0.14 (>16.0) | 0.56 (4.0) | <0.14 (>16.0) |
| Ex. 8 | 2.24 | 1.68 (1.3) | <0.14 (>16.0) | <0.14 (>16.0) | 0.56 (4.0) | 0.14 (16.0) |

[a]Data represent average of two replicates
[b]Data represent average of three replicates Referring to the data in Table V, it is noted that every invention compound had a substantially higher safety factor in sugarbeets than all prior art compounds. Particular attention is directed to the safety factors of the compounds of Examples 1, 3 and 6-8 which range from 2.2 to more than 16 times greater than those of the prior art compounds. Moreover, in addition to possessing grass, blackgrass and yellow foxtail. The results of that test (representing the average of two replicate runs) are shown in Table VI; observations were made about 18 days after treatment; selectivity factors are shown in parentheses below the $GR_{85}$ rates for each weed.

TABLE VI

| Compound | GR$_{15}$ Rate (Kg/Ha) Sugarbeets | GR$_{85}$ Rates (Kg/Ha) | | | | |
|---|---|---|---|---|---|---|
| | | WO | BYG | LCG | BG | YFT |
| Ex. 1 | <1.12 | 0.35 (>3.2) | <0.14 (>8.0) | <0.14 (>8.0) | <0.14 (>8.0) | <0.14 (>8.0) |
| I | <0.28 | ~0.99 (NS) | <0.14 (~2.0) | <0.14 (~2.0) | 0.21 (~1.3) | <0.14 (~2.0) |
| J | <0.21 | 0.28 (NS) | <0.14 (~1.5) | <0.14 (~1.5) | 0.21 (NS) | <0.14 (~1.5) |

The outstanding superiority of the compound of Example 1 relative to Compounds I and J is manifest from the standpoint of crop safety factor and selectivity against every weed in the test; Compound J was non-selective against wild oats and blackgrass and Compound I was non-selective against wild oats and narrowly selective against blackgrass in sugarbeets.

In one test, the compound of Example 1 and Compounds I and J were further tested against downy brome (DB), redroot pigweed (RRP) and annual rye (AR) in sugarbeets at application rates within the range of 0.07 to 1.12 kg/ha (0.0625 to 1.0 lb/A); observations were made 18 days after treatment; the results of that test are shown in Table VII; selectivity factors are noted in parentheses under each weed.

TABLE VII

| Compound | GR$_{15}$ Rate (Kg/Ha) Sugarbeets | GR$_{85}$ Rates (Kg/Ha) | | |
|---|---|---|---|---|
| | | DB | RRP | AR |
| Ex. 1 | ≧1.12 | 0.07 (≧16.0) | >1.12 (—) | <0.09 (≧12.0) |
| I | | 0.07 (NS) | <0.14 (1.0) | 0.07 (NS) 0.28 (NS) |
| J | <0.07 | <0.09 (NS) | <0.07 (—) | <0.07 (—) |

The test data show that prior art Compounds I and J were injurious to sugarbeets at rates as low as 0.07 kg/ha or lower and that Compound I was non-selective against downy brome and annual rye, whereas Compound J was non-selective against downy brome and of marginal or indeterminate rates below 0.07 kg/ha. In contrast, the compound of Example 1 was safe on sugarbeets at 1.12 kg/ha (maximum test rate) while selectively controlling downy brome and annual rye with selectivity factors of about 16 and 12 respectively, albeit control of redroot pigweed was marginal or indeterminate above 1.12 kg/ha.

A further test was conducted in the greenhouse to compare invention compounds of Examples 2 and 5 with Compounds K and D, respectively, i.e., the most closely-related compounds of the prior art. Example 2 and Compound K are characterized by having an isopropyl radical in one ortho position, an alkoxy radical in the other ortho position and alkoxyalkyl radical on the anilide nitrogen atom. Compound D and the compound of Example 5 are characterized by having alkenyloxymethyl radicals attached to the nitrogen atom and a methyl radical in one ortho position. The herbicides were applied to the plants at rates within the range of 0.07 to 1.12 kg/ha; observations were made 19 days after treatment; the results are shown in Table VIII.

TABLE VIII

| Compound | GR$_{15}$ Rate (Kg/Ha) Sugarbeets | GR$_{85}$ Rates (Kg/Ha) | | | | |
|---|---|---|---|---|---|---|
| | | WO | BYG | LCG | BG | YFT |
| Ex. 2 | >1.12 | 0.14 (>8.0) | <0.07 (>16.0) | <0.07 (>16.0) | 0.24 (>4.7) | <0.07 (>16.0) |
| K | 0.19 | 0.07 (2.7) | <0.07 (2.7) | <0.07 (2.7) | 0.49 (NS) | <0.07 (2.7) |
| Ex. 5 | 1.12 | 0.14 (8.0) | <0.07 (>16.0) | <0.07 (>16.0) | 0.78 (1.4) | 0.09 (11.1) |
| D | 0.19 | 0.19 (1.0) | <0.07 (>2.7) | <0.07 (>2.7) | 0.56 (NS) | <0.07 (>2.7) |

Reference to the data in Table VIII clearly shows the outstanding superiority of the invention compounds vis-a-vis Compounds D and K. In particular, the compounds of Examples 2 and 5 were safe on sugarbeets at rates of 1.12 kg/ha and higher, whereas Compounds D and K had GR$_{15}$ rates of only 0.19 kg/ha. Additionally, the selectivity factors of the invention compounds exceeded by several fold the selectivity factors of the prior art compounds against every weed in the test in sugarbeets; the prior art compounds were non-selective against blackgrass in sugarbeets.

Other tests were conducted to demonstrate the superior herbicidal properties of other compounds according to this invention. In a series of greenhouse tests, the compounds of Examples 9-12 were tested against wild oats, barnyardgrass, large crabgrass, blackgrass and yellow foxtail in sugarbeets; the results of these tests are shown in Table IX.

TABLE IX

| Compound | GR$_{15}$ Rate (Kg/Ha) Sugarbeets | GR$_{85}$ Rates (Kg/Ha) | | | | |
|---|---|---|---|---|---|---|
| | | WO | BYG | LCG | BG | YFT |
| Ex. 9[a] | 1.0 | 0.55 (1.8) | <0.14 (7.1) | <0.14 (7.1) | 0.19 (5.2) | <0.14 (7.1) |
| Ex. 10[b] | >1.12 | 0.34 (>3.3) | <0.14 (>8.0) | <0.14 (>8.0) | <0.14 (>8.0) | <0.14 (>8.0) |
| Ex. 11[c] | >1.12 | 0.19 (>5.9) | <0.14 (>8.0) | <0.14 (>8.0) | <0.14 (>8.0) | <0.14 (>8.0) |
| Ex. 12 | >1.12 | 0.84 (>1.3) | <0.14 (>8.0) | 0.14 (>8.0) | 0.14 (>8.0) | 0.14 (>8.0) |

[a]Data represent the average of four replicate tests
[b]Data represent the average of two replicate tests
[c]Data represent the average of three replicate tests Again, the superior preemergence herbicidal activity of compounds according to this invention were demonstrated both on an absolute basis and relative to the performance of relevant prior art compounds as shown in Tables IV-VIII with respect to crop safety factors, unit activities, weed control and crop/weed selectivity factors.

As noted above, data for compounds tested in plural runs was taken from tests with herbicide application rates within the range of 0.14 to 1.12 kg/ha (0.125 to 1.0 lb/A). However, additional tests with selected invention compounds have shown sugarbeet safety at rates of at least 4.48 kg/ha and selective control of various weeds at rates as low as 0.07 kg/ha. For example, the compound of Example 1 has exhibited selective control of the more-resistant weeds blackgrass and downy brome and less-resistant weeds barnyardgrass, large crabgrass, yellow foxtail and annual rye at rates as low as 0.07 kg/ha and lower. Similarly, other compounds according to this invention have also controlled one or more of the above less-resistant weeds at 0.07 kg/ha.

1.8″ (4.57 cm). Observations were made 6 weeks after treatment.

TABLE XI

| Compound | Application Mode | Rate (Kg/Ha) | Percent Inhibition | | | | | | | | | |
|---|---|---|---|---|---|---|---|---|---|---|---|---|
| | | | Tomato | Cucumber | Bush Bean | Peanut | Cotton | Soybean | Sugar beet | Rape | Foxtail (Spp) | Barnyardgrass | White Proso Millet |
| Ex. 1 | S.A. | 0.58 | 0 | 0 | 0 | 0 | 0 | 0 | 0 | 0 | 33 | 33 | |
| | | 1.12 | 0 | 0 | 0 | 0 | 0 | 0 | 0 | 0 | 82 | 82 | 20 |
| | | 2.24 | 0 | 10 | 0 | 0 | 0 | 0 | 0 | 0 | 93 | 93 | |
| | | 4.48 | 7 | 0 | 3 | 0 | 0 | 0 | 0 | 0 | 93 | 93 | 100 |
| | P.P.I. | 0.58 | 0 | 0 | 0 | 0 | 0 | 0 | 0 | 0 | 63 | 63 | 25 |
| | | 1.12 | 5 | 0 | 3 | 0 | 3 | 0 | 3 | 0 | 75 | 85 | 17 |
| | | 2.24 | 5 | 5 | 0 | 0 | 0 | 0 | 0 | 0 | 90 | 98 | 50 |
| | | 4.48 | 43 | 40 | 17 | 3 | 13 | 0 | 8 | 0 | 97 | 97 | 73 |

In a field test of relative sugarbeet safety and weed control performance, the compound of Example 1 and prior art Compounds C, E and M were tested against barnyardgrass and green foxtail under surface application ("SA") and pre-plant incorporated ("PPI") conditions at rates within the range of 1.12 to 4.48 kg/ha. Treatments were applied on a Ray silt loam soil with 1.8% organic matter; conditions were relatively dry since only 0.18 in. (0.03 cm) rain fell within the first 7 days after treatment; results of the field test are shown in Table X.

TABLE X

| Compound | Rate (Kg/Ha) | Percent Inhibition | | | | | |
|---|---|---|---|---|---|---|---|
| | | Sugarbeets | | Barnyardgrass | | Green Foxtail | |
| | | PPI | SA | PPI | SA | PPI | SA |
| Ex. 1 | 1.12 | 0 | 0 | 85 | 27 | 85 | 57 |
| | 2.24 | 10 | 3 | 92 | 48 | 92 | 65 |
| | 4.48 | 12 | 13 | 98 | 78 | 98 | 85 |
| C | 1.12 | 10 | 5 | 78 | 42 | 88 | 77 |
| | 2.24 | 22 | 18 | 87 | 77 | 93 | 87 |
| | 4.48 | 57 | 25 | 98 | 90 | 98 | 88 |
| E | 1.12 | 30 | 30 | 87 | 68 | 88 | 85 |
| | 2.24 | 80 | 63 | 100 | 95 | 100 | 95 |
| | 4.48 | 100 | 90 | 100 | 98 | 100 | 97 |
| M | 1.12 | 15 | 15 | 95 | 40 | 95 | 62 |
| | 2.24 | 30 | 23 | 100 | 78 | 100 | 85 |
| | 4.48 | 63 | 45 | 100 | 93 | 100 | 92 |

Referring to the data in Table X it is noted that of all the compounds tested, only that of Example 1 was safe (i.e., injury up to 15%) on sugarbeets at rates up to at least 4.48 kg/ha (maximum test rate), while exhibiting selective control of both barnyardgrass: and reen foxtail at 1.12 kg/ha under PPI conditions; none of the prior art compounds selectively controlled either weed even at 2.24 kg/ha; Compound M did selectively control both weeds under PPI conditions at the 1.12 kg/ha rate, but this a narrow margin of crop tolerance.

The compound of Example 1 was also tested in the field to determine its preemergence selectivity against foxtail (spp), barnyardgrass and white proso millet in a plurality of crops; the date (representing three replicate runs) are shown in Table XI for both surface application (SA) and soil incorporation (PPI, i.e., preplant incorporation) of the herbicide. The seeds were planted in a fine seedbed of silt loam of intermediate moisture. The seeds were planted at a depth of two inches (5.08 cm). First rainfall (0.2″, 0.51 cm) occurred the day following treatment, the second rain (0.25″; 0.64 cm) 2 days after treatment; cumulative rainfall 22 days after treatment was The data in Table XI show that the compound of Example 1 performed generally equivalently under both SA and PPI conditions at rates up to 4.48 kg/ha (except in tomato, cucumber and proso millet at 4.48 kg/ha PPI and against foxtails and barnyardgrass at 0.58 kg/ha). More particularly, under SA conditions, the compound of Example 1 selectively controlled foxtails and barnyardgrass in all test crops at rates from slightly above 1.12 kg/ha and proso millet at 4.48 kg/ha. Under PPI conditions, barnyardgrass was selectively controlled at 1.12 kg/ha and foxtails between 1.12 and 2.24 kg/ha, with crop safety up to 4.48 kg/ha for all crops, except tomato, cucumber and bush beans.

A distinct advantage of a herbicide is its ability to function in a wide variety of soil types. Accordingly, data is presented in Table XII showing the comparative herbicidal effect of the compound of Example 1 and Compounds C and M on various annual grasses in sugarbeets in a wide variety of soil types of varying organic matter and clay content. In these tests, pots were filled with Ray silt loam soil, compacted to a 0.375 inch (0.95 cm) from the pot surface, then seeded with sugarbeets, wild oats, barnyardgrass, large crabgrass, blackgrass and yellow foxtail. The seeds were covered, respectively, with 0.5 inch (0.127 cm) of Ray silt loam, Florida muck, Florida sand, Wabash silty clay loam, Drummer silty clay loam or Sarpy silty clay loam soil. Each herbicide was applied with a belt sprayer at 20 gpa (187 l/ha), 30 psi (2.11 kg/cm$^2$) as a surface application. Each pot received 0.25 inch (0.64 cm overhead irrigation before placing on greenhouse benches for subsequent subirrigation. Observations were made 15 days after treatment. The results of the soil tests, representing the averages of 2 replicate runs, are shown in Table XII; selectivity factors are shown in parentheses after the GR$_{85}$ rates for the weeds. Soil type composition was as follows:

| Soil Type | Percent | | | | |
|---|---|---|---|---|---|
| | Organic Matter | Clay | Silt | Sand | pH |
| Ray silt loam | 1.2 | 6.4 | 74.8 | 18.8 | 6.5 |
| Florida muck | 22.1 | NA$^a$ | NA$^a$ | NA$^a$ | 5.2 |
| Florida (Leon) sand | 2.3 | 1.8 | NA$^a$ | NA$^a$ | 6.1 |
| Drummer silty loam | 3.6 | 12.4 | 52.8 | 34.8 | 7.0 |
| Wabash clay | 2.7 | 44.4 | 34.8 | 20.8 | 6.2 |

$^a$Not available

TABLE XII

| Soil Type and Compound | GR$_{15}$ Rate (Kg/Ha) Sugarbeets | GR$_{85}$ Rates (Kg/Ha) | | | | |
|---|---|---|---|---|---|---|
| | | Wild Oats | Barnyard-grass | Large Crab-grass | Blackgrass | Yellow Foxtail |
| Ray silt loam | | | | | | |
| Ex. 1 | 2.24 | 1.12 (2.0) | <0.14 (>16.0) | <0.14 (>16.0) | 0.14 (>16.0) | <0.14 (>16.0) |
| C | 0.56 | 1.12 (NS) | <0.14 (>4.0) | 0.14 (>4.0) | 0.14 (4.0) | <0.14 (>4.0) |
| M | 0.28 | 1.12 (NS) | <0.14 (>2.0) | 0.14 (2.0) | 0.56 (NS) | <0.14 (>2.0) |
| Florida muck | | | | | | |
| Ex. 1 | >2.24 | >2.24 (—) | >2.24 (—) | >2.24 (—) | >2.24 (—) | 2.24 (>1.0) |
| C | >2.24 | >2.24 (—) | >2.24 (—) | 2.24 (>1.0) | >2.24 (—) | 2.24 (>1.0) |
| M | >2.24 | >2.24 (—) | >2.24 (—) | >2.24 (—) | >2.24 (—) | >2.24 (—) |
| Florida sand | | | | | | |
| Ex. 1 | >2.24 | >2.24 (—) | 1.12 (>2.0) | 1.12 (>2.0) | >2.24 (—) | 1.07 (>2.1) |
| C | 1.12 | 2.24 (NS) | 2.24 (NS) | 1.12 (1.0) | >2.24 (NS) | 1.12 (1.0) |
| M | 1.12 | >2.24 (NS) | >2.24 (NS) | 2.24 (NS) | >2.24 (NS) | 0.56 (2.0) |
| Wabash clay | | | | | | |
| Ex. 1 | >2.24 | 1.12 (>2.0) | 0.21 (>10.7) | <0.14 (>16.0) | 0.23 (>9.7) | 0.21 (>10.7) |
| C | 0.38 | 1.12 (NS) | 0.14 (2.7) | 0.56 (NS) | 0.56 (NS) | <0.14 (2.7) |
| M | 0.38 | 1.12 (NS) | 0.14 (2.7) | 0.28 (1.4) | 1.68 (NS) | 0.14 (2.7) |
| Drummer silt loam | | | | | | |
| Ex. 1 | 0.56 | 2.24 (NS) | 0.52 (1.1) | 0.56 (1.0) | 2.24 (NS) | 0.43 (1.3) |
| C | 1.12 | 1.12 (1.0) | 0.28 (4.0) | 0.56 (2.0) | 1.12 (1.0) | 0.28 (4.0) |
| M | 1.68 | >2.24 (NS) | 0.28 (>6.0) | 0.96 (>1.8) | >2.24 (NS) | 0.56 (>3.0) |

Reference to the data in Table XII will show that the compound of Example 1 exhibited outstandingly superior sugarbeet safety and selectivity factors higher than Compounds C and M against every weed (but for two minor exceptions) in three of the five soils, i.e., in Ray silt loam, Florida sand and Wabash clay. In more particular, the compound of Example 1 was the only compound to selectively control wild oats in Ray silt loam and Wabash clay, barnyardgrass in Florida sand and blackgrass in Wabash clay. The results were rather indeterminant in Florida muck (22.1% organic matter) at the test rate, but indicate that high organic matter soils tend to decrease activity of each of the test compounds. The compound of Example 1 did not perform as well in Drummer silt loam as the prior art compounds, but did exhibit overall higher activity across a range of soil types.

Laboratory tests were conducted to determine the relative resistance of herbicides according to the invention and prior art compounds to leaching into the soil and resulting herbicidal efficacy. In these tests, the compound of Example 1 and Compounds C and M were formulated in acetone and then sprayed at different concentrations onto a weighed amount of Ray silt loam contained in pots having filter paper covering drainage holes in the pot bottoms. The pots containing the treated soil were subjected to leaching by placing on a turntable which rotated under two nozzle tips of a water container calibrated to deliver one inch (2.5 cm) of water per hour simulating rainfall. Leaching rates were adjusted by varying the amount of time on the turntable. Water was delivered to the soil in the pots and allowed to percolate through the filter paper and drainage holes. The pots were then allowed to sit for seven days at ambient room temperature. The treated soil in the pots was then removed, crumbled and placed as a surface layer on top of other pots containing Ray silt loam soil seeded with sugarbeet, wild oat, barnyardgrass, crabgrass, blackgrass and yellow foxtail seeds. The pots were then placed on greenhouse benches, sub-irrigated and allowed to grow for 2 weeks. Visual ratings of percent growth were recorded; the data for the test compounds represent averages of two replications; test data are shown in Table XIII; abbreviations for the weeds are as in previous tables.

TABLE XIII

| Compound | Rate (Kg/Ha) | Rain (Cm) | Percent Inhibition | | | | | |
|---|---|---|---|---|---|---|---|---|
| | | | Sugarbeet | WO | BYG | LCG | BG | YFT |
| Ex. 1 | 2.24 | 0 | 10 | 100 | 100 | 100 | 100 | 100 |
| | | 1.27 | 15 | 100 | 100 | 100 | 100 | 100 |
| | | 2.54 | 10 | 100 | 100 | 100 | 100 | 100 |
| | | 5.08 | 10 | 95 | 100 | 100 | 100 | 100 |
| | | 10.16 | 10 | 75 | 100 | 85 | 90 | 95 |
| | 0.56 | 0 | 0 | 95 | 100 | 100 | 100 | 100 |
| | | 1.27 | 0 | 95 | 100 | 100 | 100 | 100 |
| | | 2.54 | 0 | 95 | 100 | 100 | 100 | 100 |
| | | 5.08 | 0 | 85 | 100 | 95 | 95 | 100 |
| | | 10.16 | 0 | 30 | 75 | 20 | 20 | 50 |
| | 0.14 | 0 | 0 | 85 | 100 | 95 | 95 | 100 |
| | | 1.27 | 0 | 85 | 100 | 95 | 95 | 100 |
| | | 2.54 | 0 | 75 | 95 | 95 | 75 | 100 |
| | | 5.08 | 0 | 50 | 95 | 85 | 75 | 95 |
| | | 10.16 | 0 | 30 | 50 | 30 | 20 | 50 |
| C | 2.24 | 0 | 30 | 100 | 100 | 100 | 100 | 100 |
| | | 1.27 | 40 | 100 | 100 | 100 | 100 | 100 |
| | | 2.54 | 40 | 95 | 100 | 100 | 95 | 100 |
| | | 5.08 | 15 | 30 | 95 | 95 | 85 | 95 |
| | | 10.16 | 0 | 20 | 75 | 50 | 20 | 50 |
| | 0.56 | 0 | 15 | 95 | 100 | 100 | 95 | 100 |
| | | 1.27 | 25 | 85 | 100 | 95 | 95 | 100 |
| | | 2.54 | 10 | 50 | 95 | 85 | 75 | 95 |
| | | 5.07 | 0 | 85 | 75 | 65 | 50 | 95 |
| | | 10.16 | 0 | 15 | 30 | 30 | 20 | 50 |
| | 0.14 | 0 | 10 | 50 | 95 | 95 | 40 | 95 |
| | | 1.27 | 0 | 30 | 95 | 85 | 40 | 85 |
| | | 2.54 | 0 | 30 | 85 | 60 | 20 | 85 |
| | | 5.08 | 0 | 30 | 65 | 40 | 20 | 75 |
| | | 10.16 | 0 | 30 | 0 | 30 | 0 | 40 |
| M | 2.24 | 0 | 40 | 85 | 100 | 100 | 95 | 100 |
| | | 1.27 | 30 | 95 | 100 | 100 | 85 | 100 |
| | | 2.54 | 20 | 85 | 100 | 100 | 60 | 100 |
| | | 5.08 | 10 | 30 | 95 | 85 | 30 | 95 |
| | | 10.16 | 10 | 30 | 60 | 50 | 15 | 50 |
| | 0.56 | 0 | 15 | 85 | 100 | 100 | 95 | 100 |
| | | 1.27 | 15 | 40 | 100 | 100 | 65 | 100 |
| | | 2.54 | 0 | 50 | 95 | 95 | 30 | 95 |
| | | 5.08 | 0 | 20 | 75 | 85 | 20 | 75 |
| | | 10.16 | 0 | 0 | 30 | 40 | 0 | 20 |
| | 0.14 | 0 | 0 | 85 | 95 | 95 | 75 | 100 |
| | | 1.27 | 0 | 50 | 95 | 85 | 60 | 95 |
| | | 2.54 | 0 | 40 | 75 | 50 | 30 | 95 |
| | | 5.08 | 0 | 0 | 60 | 30 | 20 | 60 |

TABLE XIII-continued

| Compound | Rate (Kg/Ha) | Rain (Cm) | Sugarbeet | WO | BYG | LCG | BG | YFT |
|---|---|---|---|---|---|---|---|---|
| | | 10.16 | 0 | 0 | 0 | 0 | 0 | 0 |

Percent Inhibition

Reference to the data in Table XIII will show that the compound of Example 1 was safe on sugarbeets up to at least 2.24 kg/ha and selectively controlled all weeds in the test under simulated rainfall of 10.16 cm, except wild oats which was controlled up to 7.62 cm of rain. At 2.24 kg/ha, Compounds C and M were injurious to sugarbeets until diluted with 5.08 cm of rain, under which conditions neither compound selectively controlled wild oats, nor Compound M blackgrass. At the lowest herbicide application rate (0.14 kg/ha), the compound of Example 1 selectively controlled all weeds in the test under rainfall up to 1.27 cm, and barnyardgrass, crabgrass and foxtail under 5.08 cm rainfall. In contrast, at 0.14 kg/ha, neither of Compounds C nor M selectively controlled blackgrass, nor Compound C wild oats, under any condition of rainfall and both compounds had lost selectivity against all test weeds in sugarbeet under 5.08 cm rainfall. It is thus clearly shown that the invention compound was much more resistant to leaching into the soil under varying conditions of rainfall than either of the prior art compounds, thereby providing more reliable and prolonged herbicidal activity.

Finally, in order to further demonstrate the unobvious character and unexpectedly superior properties of the invention compounds, additional preemergence herbicidal data for other compounds of similar structure, including homologs of the invention compounds, are presented in Table XIV. Compounds N-T in Table XIV are identified as follows:

N. N-(isopropoxymethyl)-2'-methoxy-6'-methyl-2-chloroacetanilide.
O. N-(isobutoxymethyl)-2'-ethoxy-2-chloroacetanilide.
P. N-(isobutoxymethyl)-2'-methoxy-2-chloroacetanilide.
Q. N-(isobutoxymethyl)-2'-methoxy-6'-methyl-2-chloroacetanilide.
R. N-(ethoxymethyl)-2'-methoxy-6'-methyl-2-chloroacetanilide.
S. N-(1-methylpropoxymethyl)-2'-methoxy-6'-methyl-2-chloroacetanilide.
T. N-(ethoxymethyl)-2'-isopropoxy-6'-methyl-2-chloroacetanilide.

compounds disclosed in said '945 and '620 patents would have generally comparable herbicidal properties. However, the completely unexpected and outstanding properties of the species of invention compounds vis-a-vis homologous and closely-related species is further demonstrated by reference to the data for Compounds N-T in Table XIV. Again, it will be noted that Compounds N-T (like other related prior art compounds as shown particularly in Tables IV-VIII) possessed very small safety factors in sugarbeets as evidenced by the low $GR_{15}$ application rates. Furthermore, none of the species in Table XIV exhibited selective control of wild oats in sugarbeets. It is also interesting to note that Compound P was non-selective against any of the weeds in the test and similarly that Compounds N, O, Q and R were completely non-selective and/or marginally selective against all weeds in the test. Of the compounds in Table XIV, only Compounds S and T exhibited selective control of barnyardgrass, crabgrass, blackgrass and yellow foxtail. However, it is again pointed out that the unacceptably low tolerance of sugarbeets to Compounds S and T coupled with non-selectivity against wild oats and narrow selectivity against the other weeds in the test make these compounds wholly unacceptable as sugarbeet herbicides. Moreover, it is noted (having reference to Tables IV--VIII) that the safety factors in sugarbeets and selectivity factors for the invention compounds in the above weeds are overwhelmingly superior to those of Compounds S and T.

Therefore, it will be appreciated from the foregoing detailed description that compounds according to this invention have demonstrated unexpected and outstandingly superior herbicidal properties both absolutely and relative to the most structurally relevant compounds, other related homologs and analogs, including commercial 2-haloacetanilides, of the prior art. More particularly, compounds of this invention have demonstrated outstanding crop safety in sugarbeets and selectivity factors particularly with respect to hard-to-kill weed species such as wild oats, blackgrass and downy brome and other problem weeds such as yellow foxtail, barnyardgrass, crabgrass, annual rye, etc., as shown in Tables II-X.

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and condi-

TABLE XIV

| Compound | $GR_{15}$ Rate (Kg/Ha) Sugarbeets | $GR_{85}$ Rate (Kg/Ha) | | | | |
|---|---|---|---|---|---|---|
| | | WO | BYG | LCG | BG | YFT |
| N[a] | <0.14 | 0.14 (NS) | <0.14 (—) | <0.14 (—) | 0.14 (NS) | <0.14 (—) |
| O | <0.14 | >2.24 (NS) | <0.14 (—) | <0.14 (—) | 1.90 (NS) | 0.14 (NS) |
| P | <0.14 | >2.24 (NS) | 0.14 (NS) | 0.14 (NS) | 0.56 (NS) | 0.28 (NS) |
| Q | <0.14 | 0.28 (NS) | <0.14 (—) | <0.14 (—) | 0.14 (NS) | <0.14 (—) |
| R | <0.07 | 0.09 (NS) | <0.07 (—) | <0.07 (—) | 0.07 (NS) | <0.07 (—) |
| S | 0.14 | 0.49 (NS) | <0.07 (>2.0) | <0.07 (>2.0) | 0.14 (1.0) | <0.14 (>1.0) |
| T[a] | 0.23 | 0.26 (NS) | <0.14 (>1.6) | <0.14 (>1.6) | 0.12 (1.9) | <0.14 (>1.6) |

[a]Data represent average of two replicates

It is pointed out that Compounds N-T, like the invention compounds of Examples 1-12, are embraced with the generic disclosure of the above-mentioned U. S. Pat. Nos. 3,442,945 and 3,547,620, but they are not specifically disclosed therein. Hence, it would be expected that the species of compounds within the genera of tioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, (cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor of anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

In another form of aqueous suspensions, a water-immiscible herbicide is encapsulated to form a microencapsulated phase dispersed in an aqueous phase. In one embodiment, minute capsules are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total composition, preferably 480 to 600 g/l. The microencapsulation process referred to here is described in more detail in the assignee's copending U.S. Ser. No. 23,566 filed Mar. 26, 1979.

Concentrates are usually solutions of active ingredient in water-immiscible or partially water-immiscible solvents together with a surface active agent. Suitable solvents for the active ingredient of this invention include dimethylformide, dimethylsulfoxide, N-methylpyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts, preferably from about 3 to 20 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-pyrazidiinium salt 5-Bromo-3-isopropyl-6-methyluracil
1,1′-Dimethyl-4,4′-bipyridinium salt

Ureas

N′-(4-chlorophenoxy)phenyl-N,N-dimethylurea N,N-dimethyl-N′-(3-chloro-4-ethylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea

Carbamates/Thiolcarbamates

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
Ethyl N,N-dipropylthiolcarbamate
S-propyl dipropylthiolcarbamate

Acetamides/Acetanilides/Anilines/Amides

2-Chloro-N,N-diallylacetamide
N,N-dimethyl-2,2-diphenylacetamide
N-(2,4-dimethyl-5-[[(trifluoromethyl)sulfonyl]amino]-phenyl)acetamide
N-Isopropyl-2-chloroacetanilide
2′,6′-Diethyl-N-methoxymethyl-2-chloroacetanilide
2′-Methyl-6′-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its $C_{1-6}$ monoalkyl amine and alkaline metal salts and combinations thereof

Ethers 2,4-Dichlorophenyl-4-nitrophenyl ether
2-Chloro-α,α,α-trifluoro-p-tolyl-3-ethoxy-nitrodiphenyl ether

Miscellaneous 2,6-Dichlorobenzonitrile
Monosodium acid methanearsonate
Disodium methanearsonate Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | Weight Percent |
|---|---|
| I. Emulsifiable Concentrates | |
| A. Compound of Example No. 1 | 50.0 |
| Calcium dodecylbenzene sulfonate/polyoxyethylene ethers blend (e.g., Atlox ® 3437F and Atlox 3438F) | 5.0 |
| Monochlorobenzene | 45.0 |
| | 100.00 |
| B. Compound of Example No. 2 | 85.0 |
| Calcium dodecyl sulfonate/alkylaryl polyether alcohol blend | 4.0 |
| $C_9$ aromatic hydrocarbons solvent | 11.0 |
| | 100.00 |
| C. Compound of Example No. 11 | 5.0 |
| Calcium dodecylbenzene sulfonate/polyoxyethylene ethers blend (e.g., Atlox 3437F) | 1.0 |
| Xylene | 94.0 |
| | 100.00 |
| II. Liquid Concentrates | |
| A. Compound of Example No. 1 | 10.0 |
| Xylene | 90.0 |
| | 100.00 |
| B. Compound of Example No. 2 | 85.0 |
| Dimethyl sulfoxide | 15.0 |
| | 100.00 |
| C. Compound of Example No. 11 | 50.0 |
| N—methylpyrrolidone | 50.0 |
| | 100.00 |
| D. Compound of Example No. 10 | 5.0 |
| Ethoxylated castor oil | 20.0 |
| Rhodamine B | .5 |
| Dimethyl formamide | 74.5 |
| | 100.00 |
| III. Emulsions | |
| A. Compound of Example No. 3 | 40.0 |
| Polyoxyethylene/polyoxypropylene block copolymer with butanol (e.g., Tergitol ® XH) | 4.0 |
| Water | 56.0 |
| | 100.00 |
| B. Compound of Example No. 4 | 5.0 |
| Polyoxyethylene/polyoxypropylene block copolymer with butanol | 3.5 |
| Water | 91.5 |
| | 100.0 |
| IV. Wettable Powders | |
| A. Compound of Example No. 5 | 25.0 |
| Sodium lignosulfonate | 3.0 |
| Sodium N—methyl-N—oleyl-taurate | 1.0 |
| Amorphous silica (synthetic) | 71.0 |
| | 100.00 |
| B. Compound of Example No. 6 | 80.0 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 7 | 10.0 |
| Sodium lignosulfonate | 3.0 |
| Sodium N—methyl-N—oleyl-taurate | 1.0 |
| Kaolinite clay | 86.0 |
| | 100.00 |
| V. Dusts | |
| A. Compound of Example No. 1 | 2.0 |
| Attapulgite | 98.0 |
| | 100.00 |
| B. Compound of Example No. 8 | 60.0 |
| Montmorillonite | 40.0 |
| | 100.00 |
| C. Compound of Example No. 9 | 30.0 |
| Bentonite | 70.0 |
| | 100.00 |
| D. Compound of Example No. 12 | 1.0 |
| Diatomaceous earth | 99.0 |
| | 100.00 |
| VI. Granules | |

-continued

| | Weight Percent |
|---|---|
| A. Compound of Example No. 1 | 15.0 |
| Granular attapulgite (20/40 mesh) | 85.0 |
| | 100.00 |
| B. Compound of Example No. 11 | 30.0 |
| Diatomaceous earth (20/40) | 70.0 |
| | 100.00 |
| C. Compound of Example No. 10 | 0.5 |
| Bentonite (20/40) | 99.5 |
| | 100.00 |
| D. Compound of Example No. 3 | 5.0 |
| Pyrophyllite (20/40) | 95.0 |
| | 100.00 |
| VII. Microcapsules | |
| A. Compound of Example No. 1 encapsulated in polyurea shell wall | 49.2 |
| Sodium lignosulfonate (e.g. Reax 88 ® B) | 0.9 |
| Water | 49.9 |
| | 100.00 |
| B. Compound of Example No. 12 encapsulated in polyurea shell wall | 10.0 |
| Potassium lignosulfonate (e.g., Reax ® C-21) | .5 |
| Water | 89.5 |
| | 100.00 |
| C. Compound of Example No. 10 encapsulated in polyurea shell wall | 80.0 |
| Magnesium salt of lignosulfate (Treax ® LTM) | 2.0 |
| Water | 18.0 |
| | 100.00 |

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usally carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective preemergence application to the plants or to the soil a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

What is claimed is:

1. Compounds of the formula

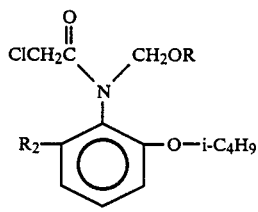

wherein
R is ethyl or n-propyl and
$R_2$ is methyl or ethyl,
said compounds being selected from the group consisting of
n-(n-propoxymethyl)-2'-isobutoxy-6'-methyl-2-chloroacetanilide and
N-(ethoxymethyl)-2'-isobutoxy-6'-ethyl-2-chloroacetanilide.

2. Compound according to claim 1 which is N-(n-propoxymethyl)-2'-isobutoxy-6'-methyl-2-chloroacetanlide.

3. Compound according to claim 1 which is N-(ethoxymethyl)-2'-isobutoxy-6'-ethyl-2-chloroacetanilide.

4. Herbicidal compositions comprising an adjuvant and a herbicidally effective amount of a compound of the formula

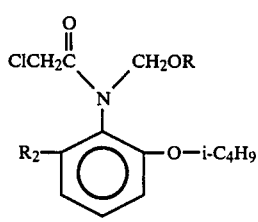

wherein
R is ethyl or n-propyl and
$R_2$ is methyl or ethyl,
said compound being selected from the group consisting of
N-(n-propoxymethyl)-2'-isobutoxy-6'-methyl-2-chloroacetanilide and
n-(ethoxymethyl)-2'-isobutoxy-6'-ethyl-2-chloroacetanilide.

5. Compositions according to claim 4 wherein said compound is N-(n-propoxymethyl)-2'-isobutoxy-6'-methyl-2-chloroacetanilide.

6. Compositions according to claim 4 wherein said compound is N-(ethoxymethyl)-2'-isobutoxy-6'-ethyl-2-chloroacetanilide.

7. Method for combatting undesirable plants associated with crop plants which comprises applying to the locus of said plants a herbicidally effective amount of a compound of the formula

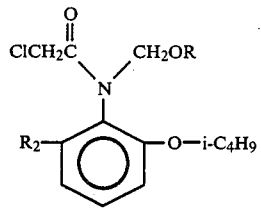

wherein

R is ethyl or n-propyl and $R_2$ is methyl or ethyl, said compounds being selected from the group consisting of N-(n-propoxymethyl-2'-isobutoxy-6'-methyl-2-chloroacetanilide and N-(ethoxymethyl)-2'-isobutoxy-6'-ethyl-2-chloroacetanilide.

8. Method according to claim 7 wherein said crop plants are sugarbeets, soybeans, cotton, peanuts, bush beans, rape, cucumber or tomato.

9. Method according to claim 8 wherein said crops are sugarbeets.

10. Method according to claim 9 wherein said compound is N-(n-propoxymethyl)-2'-isobutoxy-6'-methyl-2-chloroacetanilide.

11. Method according to claim 9 wherein said compound is N-(ethoxymethyl)-2'-isobutoxy-6'-ethyl-2-chloroacetanilide.

12. Method for combatting undesirable plants associated with sugarbeets which comprises applying to the locus thereof a herbicidally effective amount of N-(n-propoxymethyl)-2'-isobutoxy-6'-methyl-2-chloroacetanilide.

13. Method for combatting undesirable plants associated with sugarbeets which comprises applying to the locus thereof a herbicidally effective amount of N-(ethoxymethyl)-2'-isobutoxy-6'-ethyl-2-chloroacetanilide.

14. Method according to any of claims 7, 9, 10, 11, 12, or 13 wherein said undesirable plants are annual narrowleaf weeds.

* * * * *